US006986756B2

(12) United States Patent
Pelkey et al.

(10) Patent No.: US 6,986,756 B2
(45) Date of Patent: Jan. 17, 2006

(54) SINGLE USE SYRINGE AND PLUNGER ROD LOCKING DEVICE THEREFOR

(75) Inventors: Brian J. Pelkey, Rockaway, NJ (US); Steven Choon Meng Lau, Singapore (SG); Chui Khim Chua, Singapore (SG); Yaohan Moh, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 16 days.

(21) Appl. No.: 10/453,400

(22) Filed: Jun. 3, 2003

(65) Prior Publication Data

US 2004/0024357 A1 Feb. 5, 2004

Related U.S. Application Data

(63) Continuation-in-part of application No. 10/199,412, filed on Jul. 19, 2002, now abandoned.
(60) Provisional application No. 60/324,434, filed on Sep. 24, 2001.

(51) Int. Cl.
*A61M 5/00* (2006.01)
*A61M 5/315* (2006.01)

(52) U.S. Cl. ........................................ 604/110; 604/218
(58) Field of Classification Search .................. 604/110, 604/195, 218, 220, 181, 186, 187, 207–210
See application file for complete search history.

(56) References Cited

U.S. PATENT DOCUMENTS

| 2,158,593 | A | 5/1939 | Scrimgeour |
| 2,902,995 | A | 9/1959 | Loper |
| 3,179,107 | A | 4/1965 | Clark |
| 4,367,738 | A | 1/1983 | Legendre et al. ........... 128/218 |
| 4,386,606 | A | 6/1983 | Tretinyak et al. ........... 604/220 |
| 4,676,530 | A | 6/1987 | Nordgren et al. |
| 4,731,068 | A | 3/1988 | Hesse .......................... 604/110 |
| 4,758,232 | A | 7/1988 | Chak .......................... 604/220 |
| 4,781,683 | A | 11/1988 | Wozniak et al. ............ 604/110 |
| 4,781,684 | A | 11/1988 | Trenner ...................... 604/110 |
| 4,826,483 | A | 5/1989 | Molnar, IV ................. 604/110 |
| 4,840,616 | A | 6/1989 | Banks ......................... 604/110 |
| 4,961,728 | A | 10/1990 | Kosinski ..................... 604/110 |
| 4,973,310 | A | 11/1990 | Kosinski ..................... 604/110 |
| 4,978,339 | A | 12/1990 | Labouze et al. ............ 604/110 |

(Continued)

FOREIGN PATENT DOCUMENTS

| EP | 0364 777 | 4/1990 |
| EP | 1123 713 A1 | 8/2001 |
| GB | 1286690 | 8/1992 |
| GB | 2256146 | 12/1992 |
| GB | 2318060 | 4/1998 |
| WO | WO 90/03816 | 4/1990 |
| WO | WO 96/30076 | 10/1996 |
| WO | WO 97/31665 | 9/1997 |
| WO | WO 9802198 | 1/1998 |

*Primary Examiner*—Sharon Kennedy
(74) *Attorney, Agent, or Firm*—Jeanne P. Lukasavage

(57) ABSTRACT

A single use syringe assembly is provided as well as a locking element for such an assembly. The single use syringe assembly includes a barrel, a plunger rod assembly and a locking element positioned within the barrel. The locking element includes one or more barbs for engaging the inside surface of the barrel. The barbs prevent the locking element from moving proximally within the barrel, but allow its distal movement therein with the plunger rod assembly. A spring member may be provided for urging the barbs towards the inside surface of the barrel. Structure provided for holding the proximal end and the distal end of the plunger rod assembly together during normal use of the syringe is breakable upon application of an additional force applied to the proximal end of the plunger rod.

20 Claims, 18 Drawing Sheets

U.S. PATENT DOCUMENTS

| | | |
|---|---|---|
| 5,000,737 A | 3/1991 | Free et al. .................. 604/110 |
| 5,004,460 A | 4/1991 | Gimeno |
| 5,149,323 A | 9/1992 | Colonna |
| 5,181,912 A | 1/1993 | Hammett |
| 5,205,825 A | 4/1993 | Allison et al. .............. 604/110 |
| 5,205,833 A | 4/1993 | Harsh et al. |
| 5,215,524 A | 6/1993 | Vallelunga et al. |
| 5,215,536 A | 6/1993 | Lampropoulos et al. .... 604/220 |
| 5,222,942 A | 6/1993 | Bader ......................... 604/110 |
| 5,226,882 A | 7/1993 | Bates |
| 5,250,030 A | 10/1993 | Corsich ..................... 604/110 |
| 5,336,200 A | 8/1994 | Streck et al. |
| 5,383,857 A | 1/1995 | Levitov |
| 5,489,272 A | 2/1996 | Wirtz |
| 5,501,670 A | 3/1996 | Sak |
| 5,733,261 A | 3/1998 | Obong ....................... 604/110 |
| 5,738,655 A | 4/1998 | Vallelunga et al. |
| 5,814,017 A | 9/1998 | Kashmer .................... 604/110 |
| 5,833,660 A | 11/1998 | Nathan et al. |
| 5,989,219 A | 11/1999 | Villas et al. ................ 604/110 |
| 6,013,056 A | 1/2000 | Pettersen |
| 6,217,550 B1 | 4/2001 | Capes ........................ 604/110 |
| 6,283,941 B1 | 9/2001 | Schoenfeld et al. ........ 604/110 |
| 6,494,863 B1 | 12/2002 | Shaw et al. ................ 604/110 |
| 2001/0041866 A1 | 11/2001 | Capes et al. ................ 604/110 |

SINGLE USE SYRINGE AND PLUNGER ROD LOCKING DEVICE THEREFOR

This Application claims benefit and is a continuation-in-part of U.S. patent application Ser. No. 10/199,412 filed Jul. 19, 2002 now abandoned which claims priority from U.S. provisional application No. 60/324,434 filed Sep. 24, 2001.

BACKGROUND OF THE INVENTION

1. Field of the Invention

The field of the invention relates to single use syringes and locking devices for locking the plunger assemblies of such syringes.

2. Brief Description of the Related Art

In the United States and throughout the world the multiple use of hypodermic syringe products that are intended for single use only is instrumental in drug abuse and more particularly in the transfer of contagious diseases. Intravenous drug users who routinely share and reuse syringes are a high risk group with respect to the AIDS virus. Also, the effects of multiple use are a major concern in third world countries where repeated use of syringe products may be responsible for the spread of many diseases. Reuse of single use hypodermic syringe assemblies is also instrumental in the spread of drug abuse even in the absence of infection or disease.

Many attempts have been made to remedy this problem. Some of these attempts have required a specific act to destroy the syringe after use either by using a destructive device or providing a syringe assembly with frangible zones so that the syringe could be rendered inoperable by the application of force. Other attempts have involved the inclusion of structure which would allow the destruction or defeating of the syringe function through a conscious act by the syringe user. Although many of these devices work quite well, they do require the specific intent of the user followed by the actual act to destroy or render the syringe inoperable. None of these devices is effective with a user having the specific intent to reuse the hypodermic syringe.

Single use hypodermic syringes that become inoperative or incapable of further use automatically without any additional act on the part of the user have been developed. One such syringe is disclosed in U.S. Pat. No. 4,961,728. The syringe disclosed in this patent includes a locking element positioned in the syringe barrel. The locking element includes proximally and outwardly facing barbs that engage the inner surface of the syringe barrel and an inwardly facing driving edge adapted to interact with the plunger rod to move the locking element along the barrel as the stopper is advanced. The plunger rod includes a ledge positioned at a distance from the proximal side of a support wall that approximates the length of the locking element. The driving edge of the locking element engages the ledge, thereby ensuring that the locking element moves distally with the plunger rod and stopper.

U.S. Pat. Nos. 5,021,047, 5,062,833 and 5,562,623 disclose single use syringes having plunger rods that have teeth or ridges and locking elements that engage the teeth or ridges. The locking elements of these syringes also include outwardly extending teeth or prongs that engage the inside surface of the syringe barrel. The plunger rods of these syringes can be retracted to draw fluid into the syringe barrel while the locking elements remain stationary. Distal movement of the plunger rods causes the fluid to be expelled, the locking elements moving distally with the plunger rods and substantially preventing further plunger rod retraction.

SUMMARY OF THE INVENTION

A locking element for a single use syringe is provided. The locking element includes a base including a generally trough-shaped body having a longitudinal axis. A first leg extends from the base and is substantially parallel to the longitudinal axis. A second leg extends from the base in opposing relation to the first leg. Each leg includes one or more barbs. Each leg further includes an end portion that extends generally toward the longitudinal axis. A spring element is attached to the base for urging the barbs in a selected direction. The barbs are preferably located on the outer edges of the first and second legs.

A single use syringe assembly with a needle cannula in accordance with the invention includes a barrel having an inside surface defining a chamber for retaining fluid. The barrel has an open proximal end and a distal end having a passageway in communication with the chamber. A plunger rod assembly is provided for use in conjunction with the barrel. The plunger rod assembly includes an elongate body portion having a proximal end, a distal end, and a stopper mounted to the elongate body portion proximate the distal end. The stopper is slidably positioned in substantially fluid tight engagement with the inside surface of the barrel. The elongate body portion of the plunger rod assembly extends outwardly from the open proximal end of the barrel. A generally trough-shaped locking element is positioned within the barrel. The locking element defines a channel through which the elongate body portion of the plunger rod assembly extends. One or more barbs extend from the locking element. The barbs engage the inside surface of the barrel for substantially preventing the locking element from moving proximally with respect to the barrel. The locking element also engages the elongate body portion of the plunger rod assembly such that the locking element is movable towards the distal end of the barrel as the plunger rod assembly is advanced. A spring member is attached to the locking element and urges the one or more barbs towards the inside surface of the barrel.

A single use syringe assembly is further provided that includes a barrel having an inside surface defining a chamber for retaining fluid, a plunger rod assembly, a needle cannula for hypodermic injection, and a locking element. The plunger rod assembly includes an elongate body portion having a proximal end, a distal end and a stopper mounted to the elongate body portion. The stopper is slidably positioned in substantially fluid tight engagement with the inside surface of the barrel. The locking element is positioned within the barrel. It includes first and second opposing walls and a third wall that connects them. A first leg extends from the first wall and a second leg extends from the second wall. A first barb extends from the first leg of the locking element while a second barb extends from the second leg thereof. It will be appreciated that one or more barbs may extend from the legs of the locking element. Each leg includes an end portion engageable with the body portion of the plunger rod assembly. The locking element can accordingly be moved distally with the plunger rod assembly along the syringe barrel. The barbs substantially prevent the locking element from moving proximally therein.

The single-use syringe assembly of the present invention may also include additional structure wherein the proximal end of the plunger rod and the distal end of the plunger rod are connected by a breakable connection. The proximal end and/or the distal end may include an axial projection having at least one transverse protuberance projecting therefrom. The protuberance is connected to the other of the proximal and/or the distal end of the plunger rod. The breakable connection is on the protuberance and is strong enough to hold the proximal end and the distal end of the plunger rod together during normal use of the syringe and breakable upon application of an additional force applied to the proximal portion of the plunger rod. The breakable connection is preferably positioned proximally with respect to the locking element and preferably includes a plurality of transverse protuberances. The axial projection may be planar shaped having a sidewall and at least one transverse protuberance projecting from the sidewall. The proximal portion of the plunger rod, the distal portion of the plunger rod and the breakable connection may be integrally molded of plastic material. The breakable connection may be made of material selected from the group consisting of polyethylene, polystyrene, polypropylene and adhesives. The stopper and the distal end of the plunger rod may be integrally molded of plastic material. The syringe assembly may also include means for preventing the breakable connection from breaking when the additional force is distally directed and not prevent such breaking when the additional force is proximally directed.

DETAILED DESCRIPTION OF THE INVENTION

Figure 1:
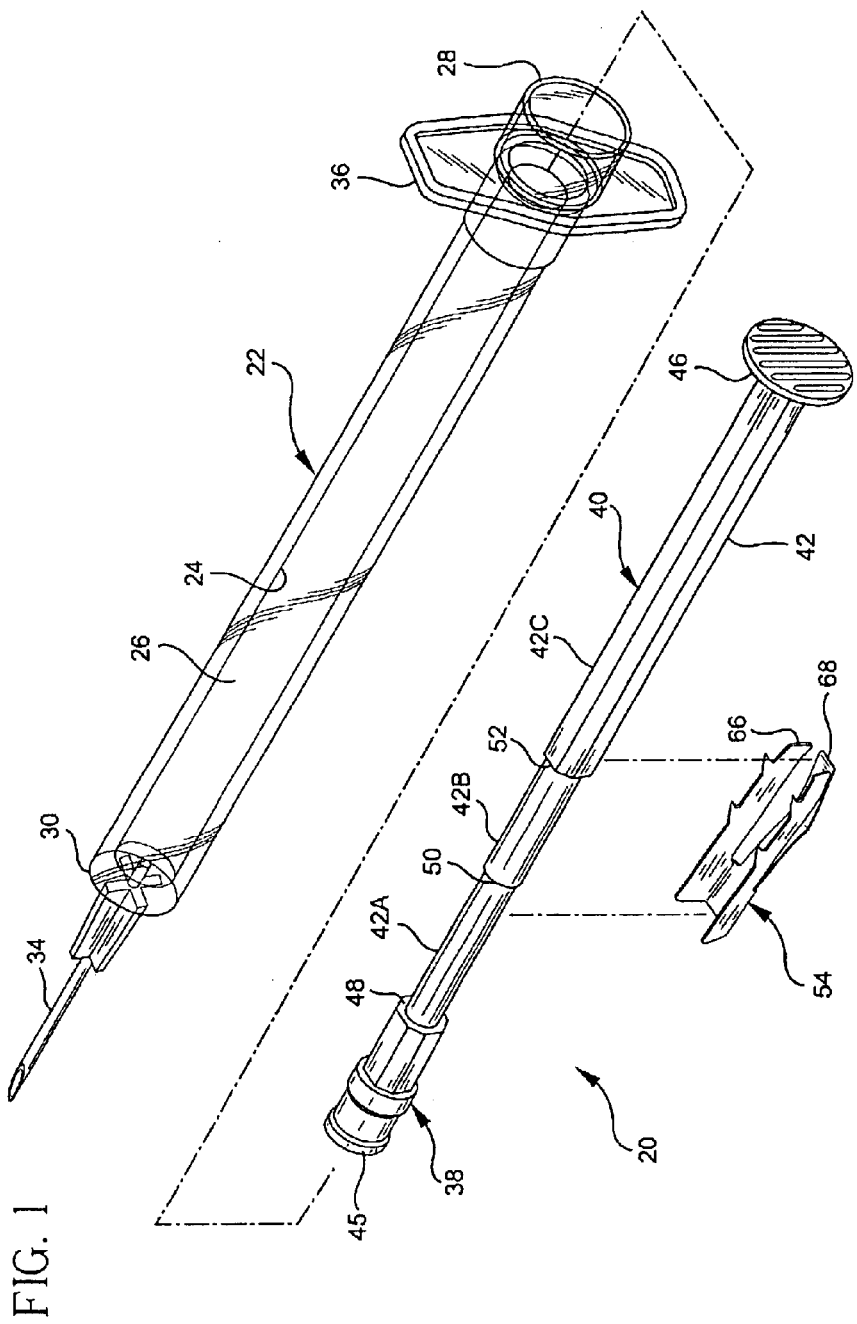
FIG. 1 is an exploded, perspective view showing a single use syringe assembly according to the invention.

There is shown in the drawings and will be described in detail herein a preferred embodiment of the invention with the understanding that the present disclosure is to be considered as exemplary of the principles of the invention and is not intended to limit the invention to the embodiment illustrated.

Figure 2:
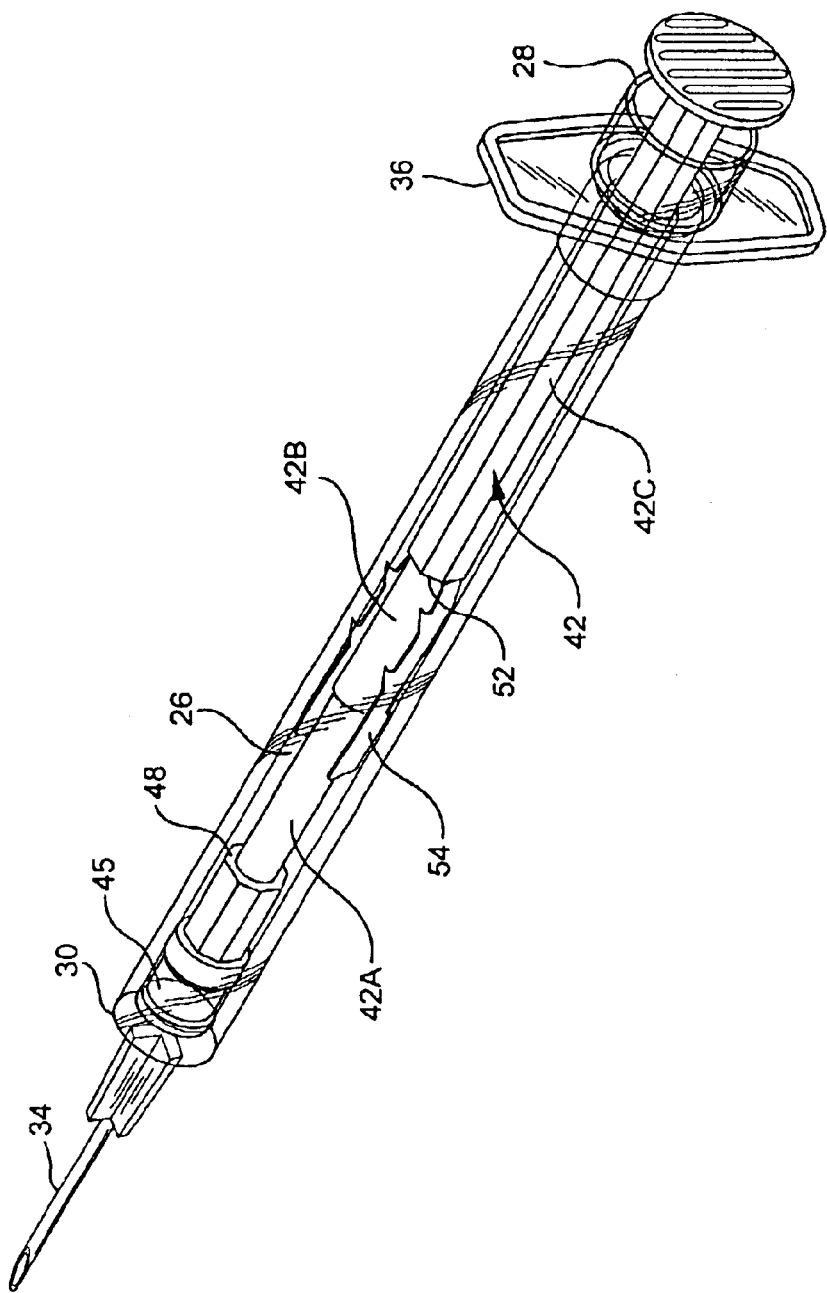
FIG. 2 is a top perspective view of the syringe assembly prior to use.
Figure 3:
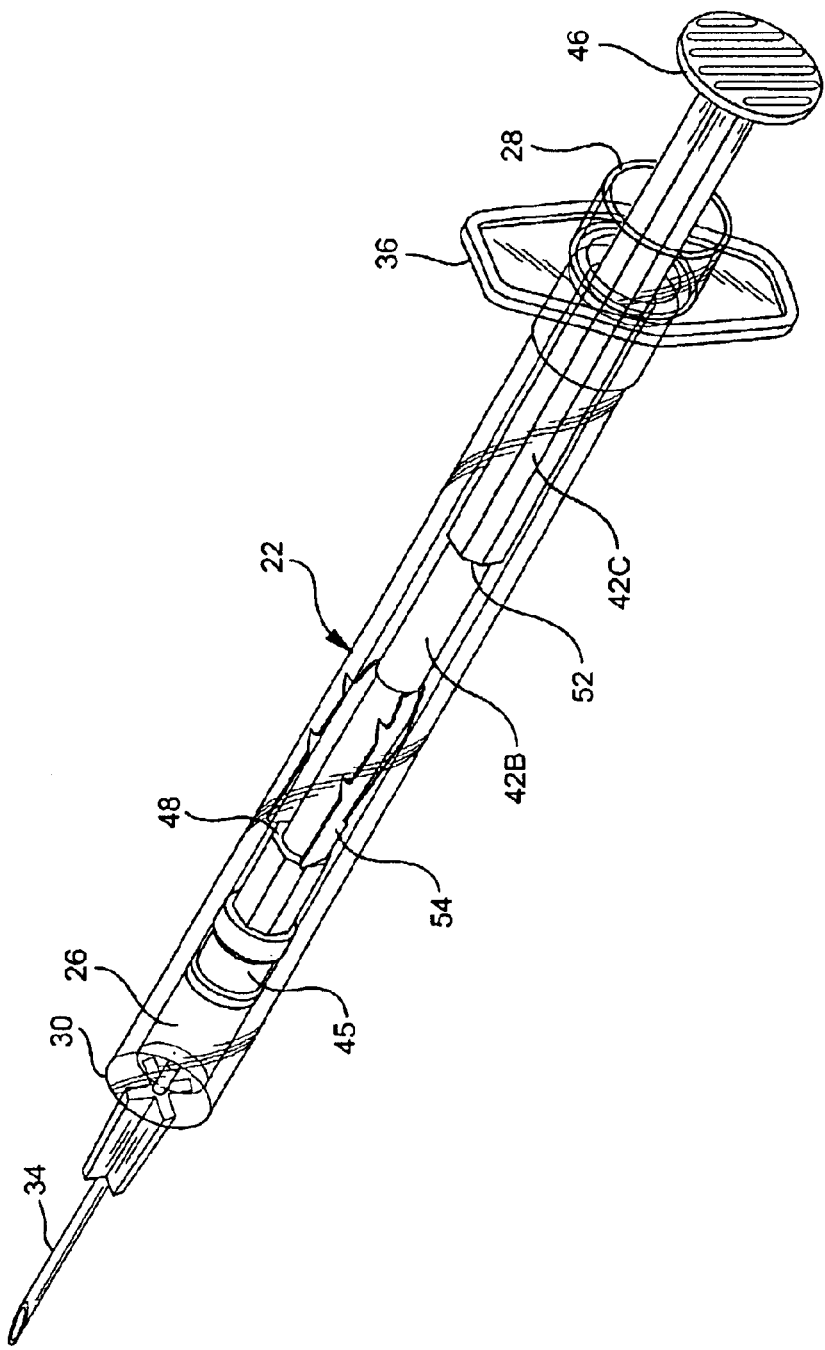
FIG. 3 is a top perspective view showing the syringe assembly following retraction of the plunger rod assembly thereof.

Referring first to FIGS. 1–3, a single use syringe assembly 20 includes a barrel 22 having an inside surface 24 defining a chamber 26 for retaining fluid. The barrel 22 includes an open end 28 and a distal end 30 having a passageway 32 therethrough in communication with the chamber. A needle cannula 34 projects outwardly from the distal barrel end. The needle cannula has a lumen (not shown) therethrough in fluid communication with the passageway and a sharpened distal tip. The syringe assembly of the present invention is preferably used with a needle cannula that is attached to the distal end of the barrel by an adhesive or other suitable means. It will be appreciated that the invention could be applied to syringe assemblies having removable needle/hub assemblies, or fixed or removable blunt cannulas.

As used in the preceding paragraph and hereafter, the term "distal end" refers to the end furthest from the person holding the syringe assembly. The term "proximal end" refers to the end closest to the holder of the syringe assembly. In the preferred embodiment, the proximal end of the barrel 22 includes a flange 36 to facilitate handling and positioning of the syringe assembly and to maintain the relative position of the barrel with respect to the plunger rod during filling and medication administration.

A plunger assembly 38 includes a plunger rod 40 having an elongate body portion 42. The distal end of the elongate body portion includes a projection having an enlarged end 44. A stopper 45 having a recess therein is affixed to this end. A disc-shaped flange 46 is provided at the proximal end of the plunger rod for allowing the user to apply the force necessary to move the plunger rod with respect to the barrel. The elongate body portion 42 includes several sections between the proximal and distal ends thereof. A first section 42A thereof is substantially cylindrical. The distal end of this section adjoins an enlarged plunger rod surface that functions as a stop surface 48 as described hereafter. A second section 42B adjoins the proximal end of the first section, and is also substantially cylindrical. The second section is larger in diameter than the first section, and accordingly defines a shoulder 50 at the proximal end of the first section. A third section 42C extends between the second section 42B and the disc-shaped flange 46. A second shoulder 52 adjoins the proximal end of the second section 42B, and separates the second and third sections.

A locking element 54 is positioned within the barrel 22. In accordance with the preferred embodiment, the locking element is generally trough-shaped. The locking element defines a channel through which the elongate body portion 42 of the plunger rod 40 extends. It will be appreciated that the locking element can be U-shaped in cross section or otherwise similarly configured, all of which should be considered generally trough-shaped as the term is used herein.

The locking element includes a base 56 that includes a bottom wall 58 and first and second opposing sidewalls 60, 62. A first leg 64 extends proximally from the first wall and a second leg 66 extends proximally from the second wall. The legs 64, 66 are also in opposing relation. A spring element 68 in the form of a third leg extends proximally from the bottom wall 58.

Figure 10:
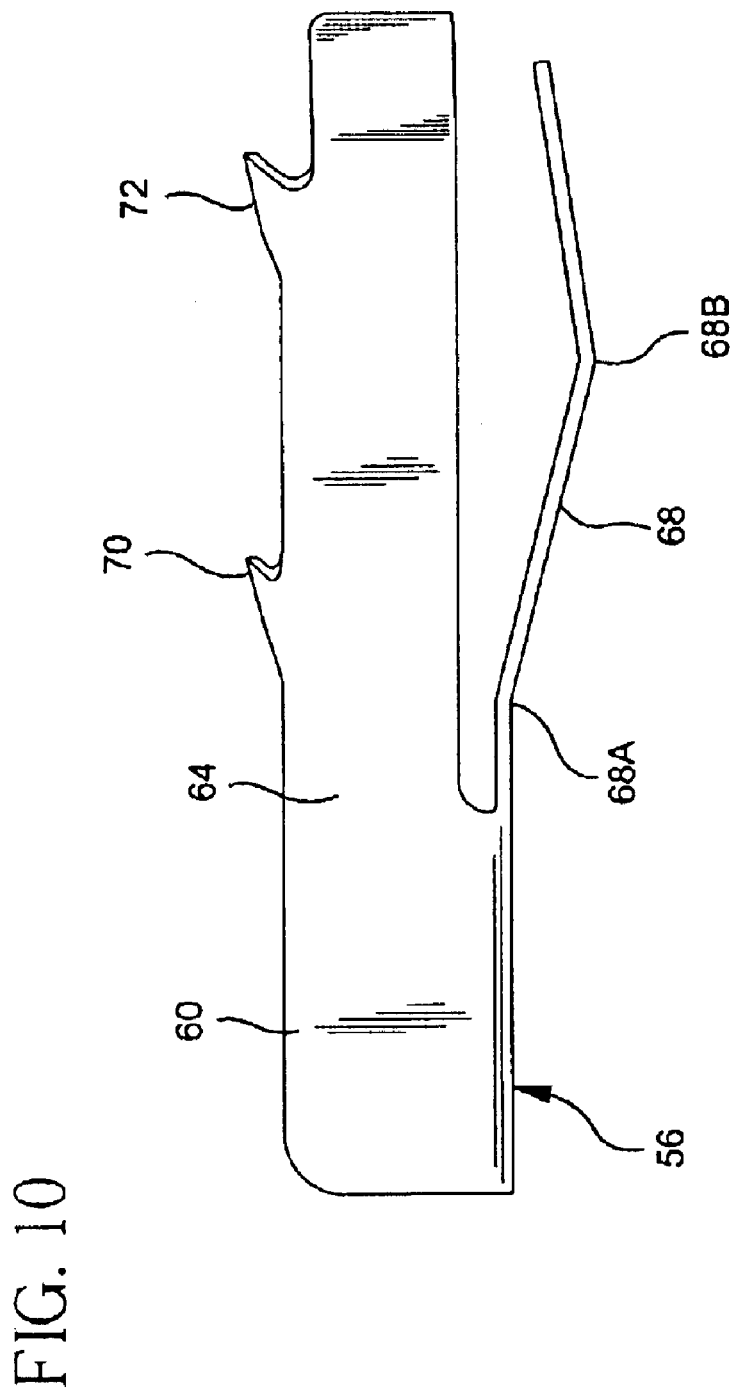
FIG. 10 is a side elevation view of the locking element.
Figure 11:
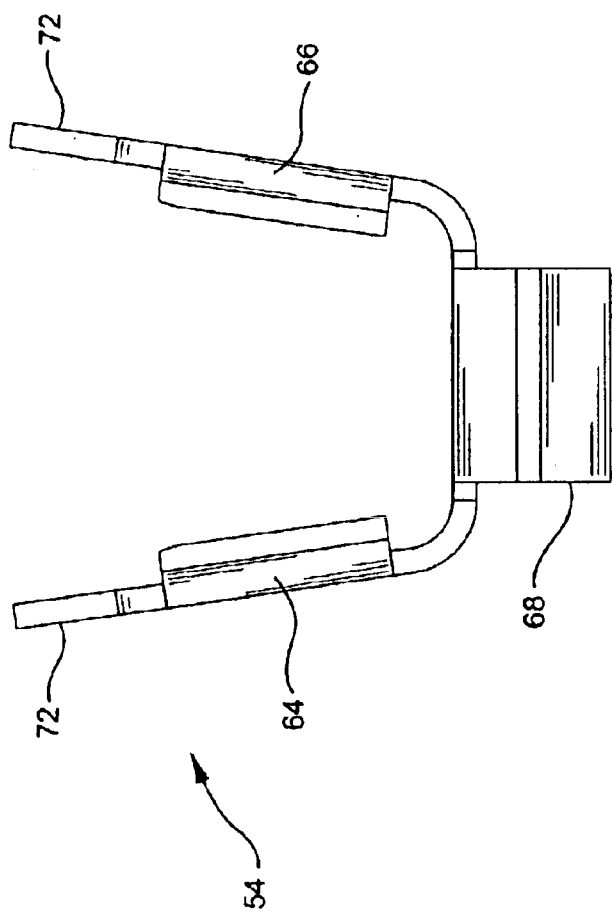
FIG. 11 is an end view of the locking element.
Figure 12:
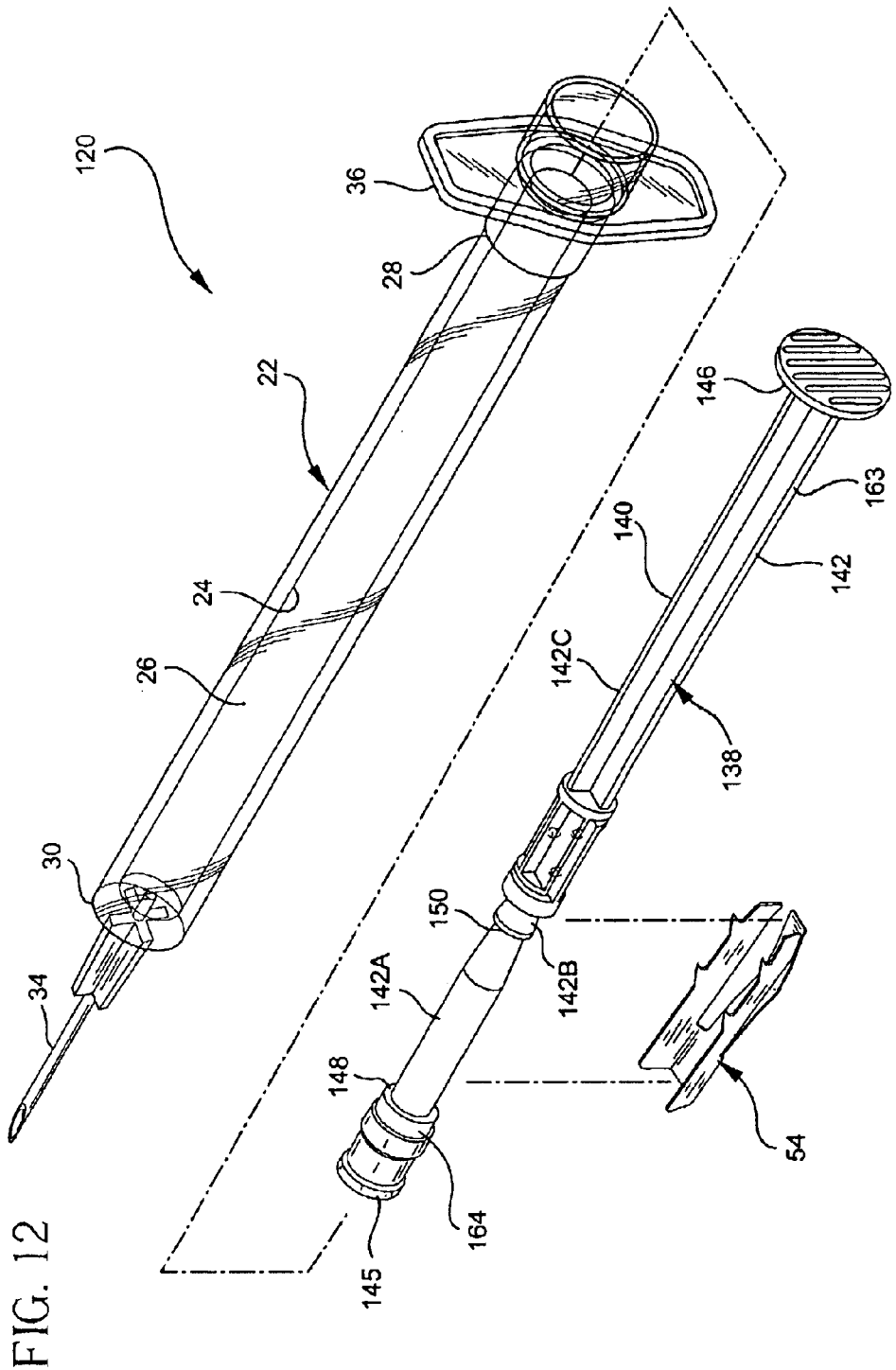
FIG. 12 is an exploded, perspective view showing another embodiment of the single-use syringe assembly of the present invention.

Each of the legs 64, 66 includes an end portion that is angled generally towards a longitudinal axis extending through the channel defined by the locking element. They further include inner and outer edges. (The terms "inner" and "outer" are relative terms as used herein.) The inner edges thereof are substantially adjacent to the spring element. Barbs 70, 72 are integral with the outer edges of the first and second legs. The spring element 68 includes a pair of bends 68A, 68B therein. It accordingly extends beneath the plane of the bottom wall 58 of the base 56, as best shown in FIG. 10.

Figure 7:
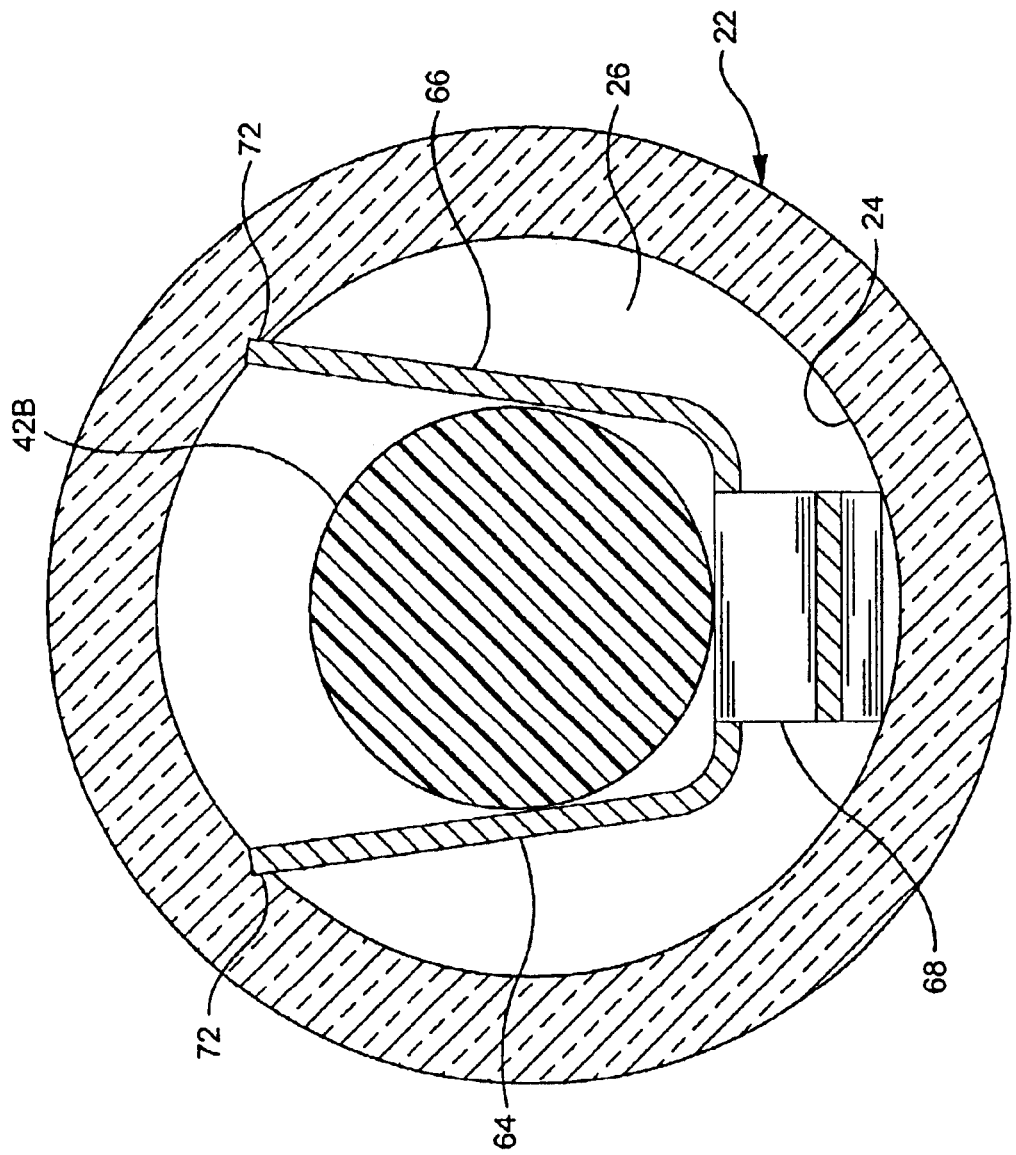
FIG. 7 is a cross-sectional view of the syringe of FIG. 4 taken along line 7—7.
Figure 8:
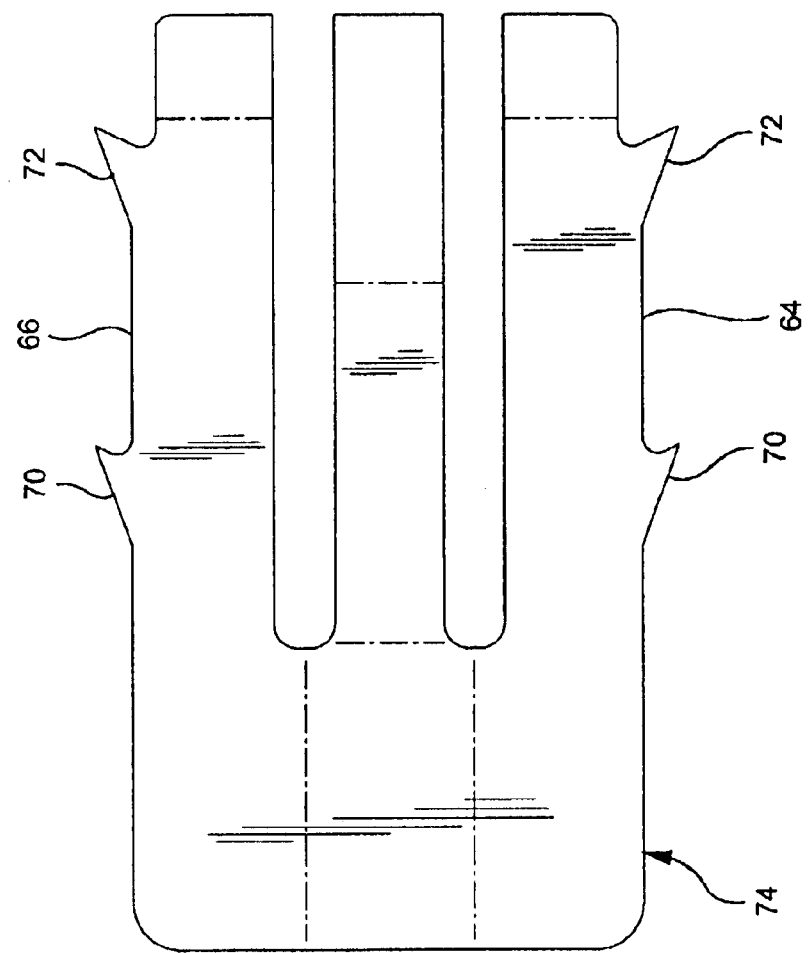
FIG. 8 is a top plan view of a preform of a locking element.
Figure 9:
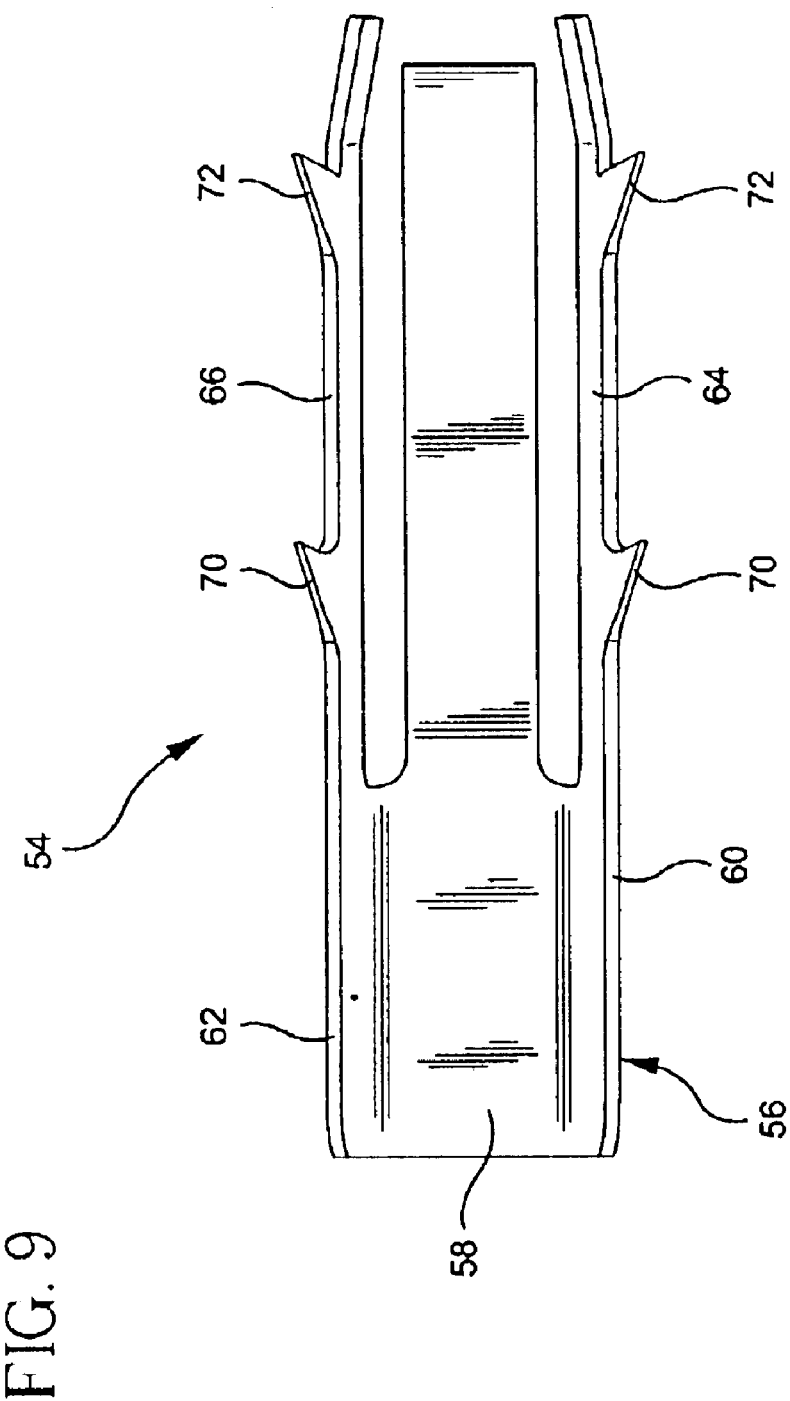
FIG. 9 is a top plan view of a locking element for the single use syringe assembly.

The locking element is preferably formed from a thin sheet of metal such as stainless steel. It is preformed into the flat configuration shown in FIG. 7. The broken lines show the folds that are made in the flat substrate 74 to form the locking element 54 shown in FIGS. 7 and 9–11. The dimensions of the locking element are selected in accordance with the barrel and plunger rod assembly with which it is to be used.

The syringe assembly is easily constructed from the component parts thereof. The locking element is positioned on the section 42B of the plunger rod 40 such that the angled end portion of the legs 64, 66 adjoin the shoulder 52 at the proximal end of this section. The legs 64, 66 and spring member extend proximally, and the barbs 70, 72 are angled proximally with respect to the plunger rod. The plunger rod/locking element assembly is then inserted into the barrel 22 through the proximal end thereof. As the assembly is moved distally within the barrel, the angular orientation of the barbs allows them to slide along while engaging the inside surface 24 of the barrel. The locking element moves distally with the plunger rod due to the engagement of the ends of the legs 64, 66 with the shoulder. The plunger rod/locking element assembly is moved distally to the positions shown in FIGS. 2 and 4 where the stopper engages the end wall of the barrel. The syringe assembly is then ready for use or storage.

Figure 4:
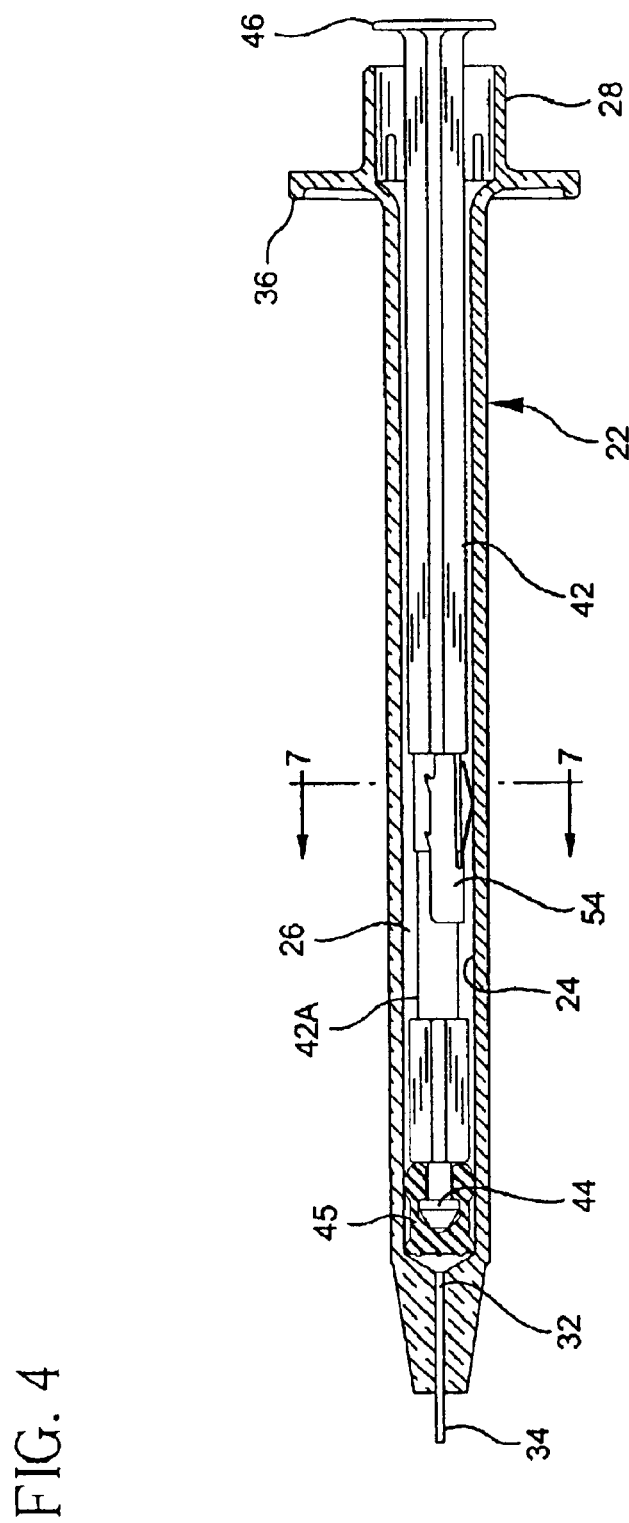
FIG. 4 is a cross-sectional view of the syringe assembly with the plunger rod assembly in the position shown in FIG. 2.
Figure 5:
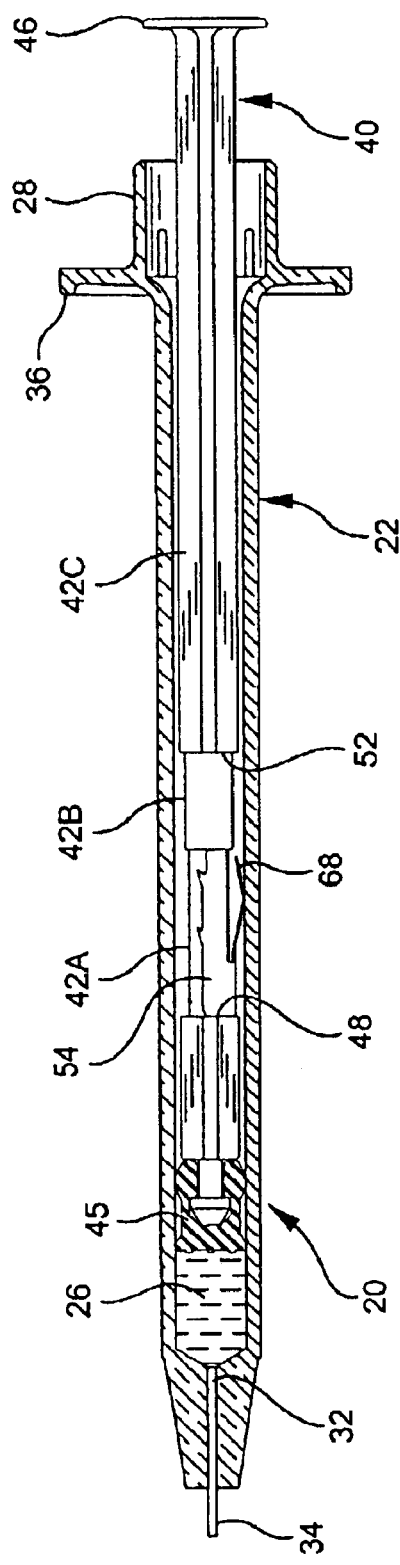
FIG. 5 is a cross-sectional view thereof showing the plunger rod assembly in the position shown in FIG. 3.

In use, the plunger rod assembly 38 is retracted from the position shown in FIG. 4 to the position shown in FIG. 5 in order to draw fluid through the needle cannula 34 and passageway 32 and into the chamber 26 of the barrel 22. The locking element 54 remains stationary during such retraction, and the plunger rod assembly is moved proximally with respect to both the barrel 22 and the locking element. This is due to the engagement of the barbs 70, 72 with the inside surface 24 of the barrel. The barbs are preferably made from a harder material than the barrel, which enhances their ability to resist proximal movement. The barbs are resiliently urged by the spring member towards the inside surface 24 of the barrel, further enhancing their effectiveness.

Retraction of the plunger rod assembly 38 is limited by the locking assembly. As shown in FIG. 5, the stop surface 48 on the plunger rod 40 engages the distal end of the locking element 54. As the locking element cannot be moved proximally, further retraction of the plunger rod assembly is not possible. The amount of fluid that can be drawn into the chamber 26 is accordingly limited by the distance between the stop surface 48 and the second shoulder 52 as well as the length of the locking element. It will be appreciated that the distance between the stop surface 48 and second shoulder 52 and the length of the locking element 54 can be chosen to meet the needs of particular applications.

The end portions of the legs 64, 66 of the locking element adjoin the first shoulder 50 when the plunger rod assembly is retracted to the position shown in FIG. 5. The distance between the first shoulder 50 and the stop surface 48, being substantially the same as the distance between the distal end of the locking element and the proximal end portions of the legs, causes the locking element to be substantially immovable with respect to the plunger rod assembly. As discussed above, the locking element is substantially immovable in the proximal direction within the barrel due to the engagement of the barbs 70, 72 with the inside surface of the barrel 22.

Figure 6:
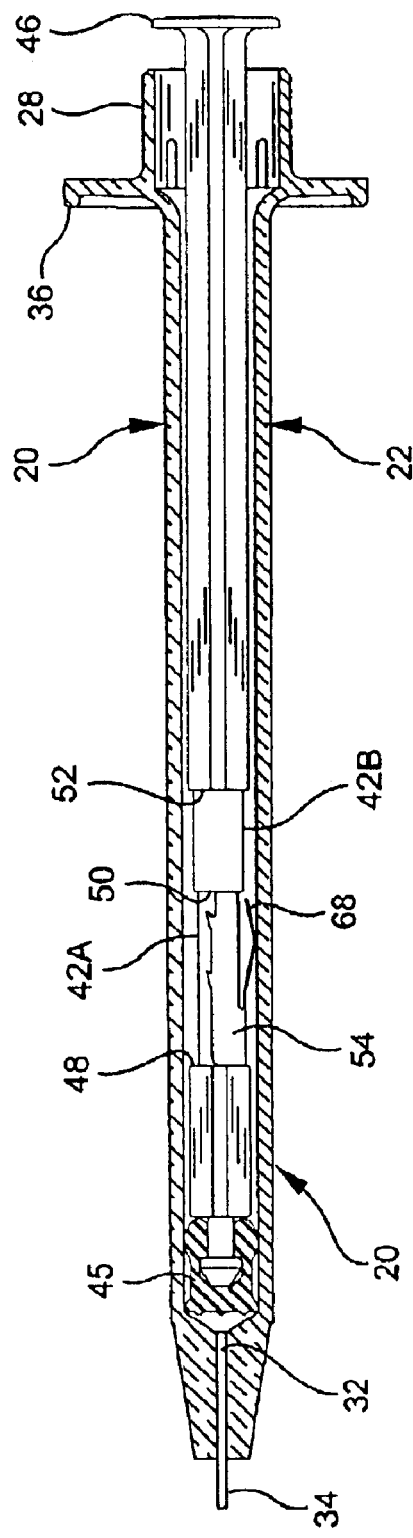
FIG. 6 is a cross-sectional view thereof showing the plunger rod assembly in a locked position following the injection stroke.

Once the fluid has been drawn into the barrel from a vial or other fluid source, the needle cannula can be removed from the fluid source and used for injection. During the injection of a patient, the plunger assembly 38 and locking element both move distally from the positions shown in FIG. 5 to the positions shown in FIG. 6. In FIG. 6, the stopper 45 again adjoins or engages the end wall of the barrel 22. The locking element 54 remains positioned between the stop surface 48 and the first shoulder 50. Both the plunger rod assembly 38 and the locking element are substantially immovable from their positions. The syringe assembly 20 accordingly cannot be reused.

The syringe barrel of the present invention may be constructed of a wide variety of rigid materials with thermoplastic materials such as polypropylene and polyethylene being preferred. Similarly, thermoplastic materials such as polypropylene, polyethylene and polystyrene are preferred for the plunger rod. A wide variety of materials such as natural rubber, synthetic rubber and thermoplastic elastomers are suitable for the stopper. The choice of stopper material will depend on compatability with the medication being used. In the preferred embodiment of this invention, the stopper 45, made of medical grade rubber, includes a partially hollow interior with an undercut ledge which is snap fit over complementary structure 44 on plunger rod 40 to secure the stopper to the plunger rod. The stopper and plunger rod may also be integrally formed of the same material or different materials, or secured together in other suitable ways.

As previously recited, it is preferable that the locking element be fabricated from a material which is harder than the barrel so that the locking barbs may effectively engage the barrel. Resilient spring like properties are also desirable along with low cost dimensionally consistent fabrication. With this in mind, sheet metal is the preferred material for the locking element with stainless steel being preferred for medical applications. Although the locking element of the preferred embodiment is fabricated from a single sheet, it is within the purview of the instant invention to include locking elements made of other forms and/or containing multiple parts and materials.

FIGS. 12–18 illustrate another alternative embodiment of the present invention. This embodiment functions similarly to the embodiment of FIGS. 1–11 and incorporates new structural features to prevent the use of excessive force applied to the plunger rod from overriding the locking element in an attempt to improperly reuse the syringe assembly.

A single-use syringe assembly 120 includes a barrel 22 having an inside surface 24 defining a chamber 26 for retaining fluid. Barrel 22 includes an open proximal end 28 and a distal end 30 having a passageway 32 therethrough in fluid communication with the chamber. A needle cannula 34 projects outwardly from the distal end of the barrel and includes a lumen (not shown) therethrough in fluid communication with the passageway.

A plunger rod assembly 138 includes a plunger rod 140 having an elongate body portion 142. The distal end of the plunger rod includes a stopper 145. A disc-shaped flange 146 is provided at the proximal end of the plunger rod for allowing the user to apply the force necessary to move the plunger rod with respect to the barrel. Elongate body portion 142 includes several sections between the proximal and distal ends thereof. The first section 142a is substantially cylindrical. The distal end of this section adjoins an enlarged plunger rod surface that functions as a stop surface 148. A second section 142b adjoins the proximal end of the first section and is substantially cylindrical. The second section is larger in diameter than the first section, and accordingly defines a shoulder 150 at the proximal end of the first section. A third section 142c extends between the second section and the disc-shaped flange. A second shoulder 152 adjoins the proximal end of the second section 142b, and separates the second and third sections. The distal end and the proximal end of the plunger rod are connected by a breakable connection illustrated in this embodiment in section 142c of the plunger rod and positioned proximally with respect to the locking element. Specifically, proximal end 163 and distal end 164 of the plunger rod are connected by a breakable connection. The breakable connection is strong enough to hold proximal end 163 and distal end 164 together during normal use of the syringe and is breakable upon application of additional force to the proximal portion along longitudinal axis 141 of the plunger rod. There can be one or more breakable connections connecting the proximal end 163 and the distal end 164.

In this embodiment proximal end 163 includes a distal projection 168 having at least one transverse protuberance projecting therefrom, and distal end 164 includes a proximal projection 169 having at least one transverse protuberance projecting therefrom. In this embodiment, there are two transverse protuberances connected to proximal end 163 and one transverse protuberance connected to distal end 164. The protuberances on the proximal end are connected to the distal end through breakable connection 171. Likewise, the protuberance on the distal end is connected to the proximal end through breakable connections 171. The breakable connection is preferably on the distal end of the protuberance. The distal projection may be circularly shaped and fit into a cylindrically shaped recess in the distal end. With this structure, a single protuberance extending up to 360° may be used. The structure may be reverse so that the projection extends proximally from the distal end toward the proximal end or there may be mutual projections joined by a breakable connection. All of these combinations fall within the purview of the present invention, and the preferred embodiment illustrating three transverse projections having three breakable connections is merely representative of these many possibilities.

In this embodiment, proximal end 163 and distal end 164 and the breakable connections are integrally molded of plastic material. A wide variety of plastic materials are suitable for molding the plunger rod with polystyrene, polypropylene and polyethylene being preferred. It is important to control the modulus of elasticity of the material selected for the transverse protuberances which are part of the breakable connection between the proximal end and the distal end of the plunger rod. The breakable connection must break or fail before the proximal end of the plunger contacts the distal end of the plunger. If the modulus is too high, the break will occur too easily, causing premature breakage. If the modulus is too low the breakable connection may not break because the proximal portion and the distal portion will contact each other to resist further relative movement between the proximal and distal ends.

A breakable connection can be anywhere along the protuberance, at its proximal end, its distal end or in between, depending on, among other things, the geometry of the protuberance. A breakable connection can also be made by connecting the protuberance to the distal end or the proximal end using a frangible adhesive. The protuberance may be made entirely or partially of adhesive or frangible material. The connection may also be made using a shear pin passing through the distal end and the proximal end. The shear pin may be made of plastic with one or more notches or stress risers suitably placed to cause breaking at the desired force levels. The breakable connection between the proximal portion and the distal portion may also be accomplished by using a snap-fit arrangement. With this latter structure, the distal portion and the proximal portion can be individually molded and snapped together during the assembly process.

Figure 18:
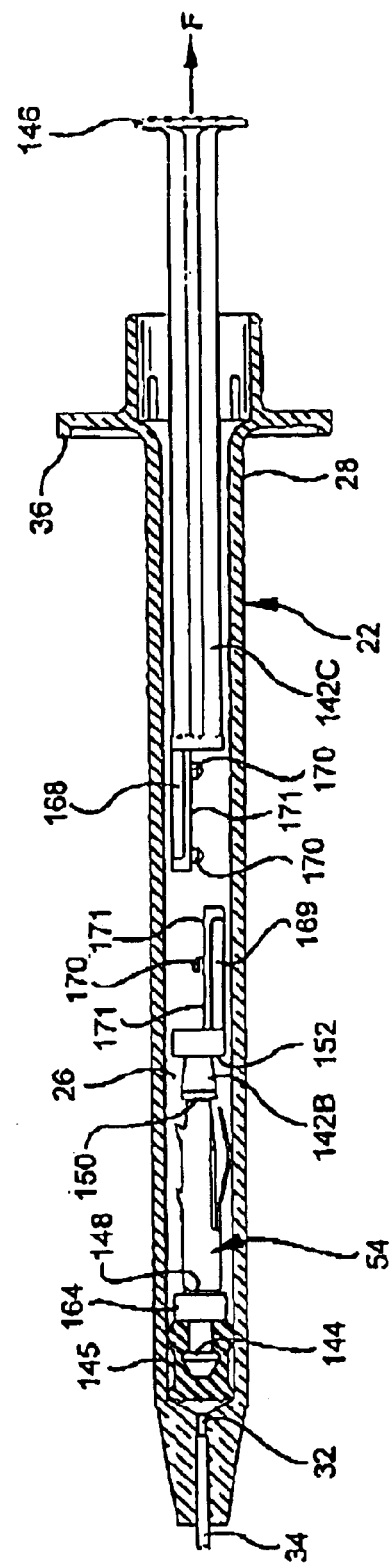
FIG. 18 is a cross-sectional side-elevational view illustrating the syringe assembly of FIG. 14 after excessive force has been applied to the plunger rod to break the breakable connections.

Also, the structure of the distal end and the proximal end of the plunger rod can be configured to allow the breakable connection to break upon a proximally directed force but not a distally directed force or vice versa. For example, a distally facing surface such as distal surface 173 on distal projection 168 can be close to or touching the distal end of the plunger rod so that upon the application of an additional distally directed force to the plunger rod, which could provide the necessary movement or deflection required for breaking a breakable connection, such breaking will be prevented by virtue of distal surface 173 contacting distal end 164 of the plunger rod. Likewise, a proximally facing surface such as proximal surface 174 on proximal projection 169 can be close to or touching proximal end 163 of the plunger rod so that movement or deflection required for breaking the breakable connection through application of a distally directed force to the plunger rod will be prevented by virtue of proximal surface 174 contacting proximal end 163 of the plunger rod. One or both of surfaces 173 and 174 can be used to prevent breaking of the breakable connection through the application of a distally directed force to the proximal end of the plunger rod. Accordingly, the breakable connection, in such configuration, can be broken by application of a proximally directed force F on the proximal end of the plunger rod as best seen in FIG. 18. Having means for allowing the breakable connection to break through application of forces in one direction but not in another is a desirable feature. For example, by only allowing the breakable connection to break upon application of a proximally directed force to the plunger rod, a breakable connection will be protected from accidental breaking due to excessive distally directed forces being applied to the plunger rod during the discharge of liquid from the barrel through the needle cannula. Also, the compact structure of the present embodiment having a single distal projection from the proximal end of the plunger rod connected to a single proximally directed projection on the distal end of the plunger rod connected by one or more breakable connections is ideally suited for syringes of small diameter where a more elaborate or complex structure would not fit in the chamber of the barrel.

Figure 13:
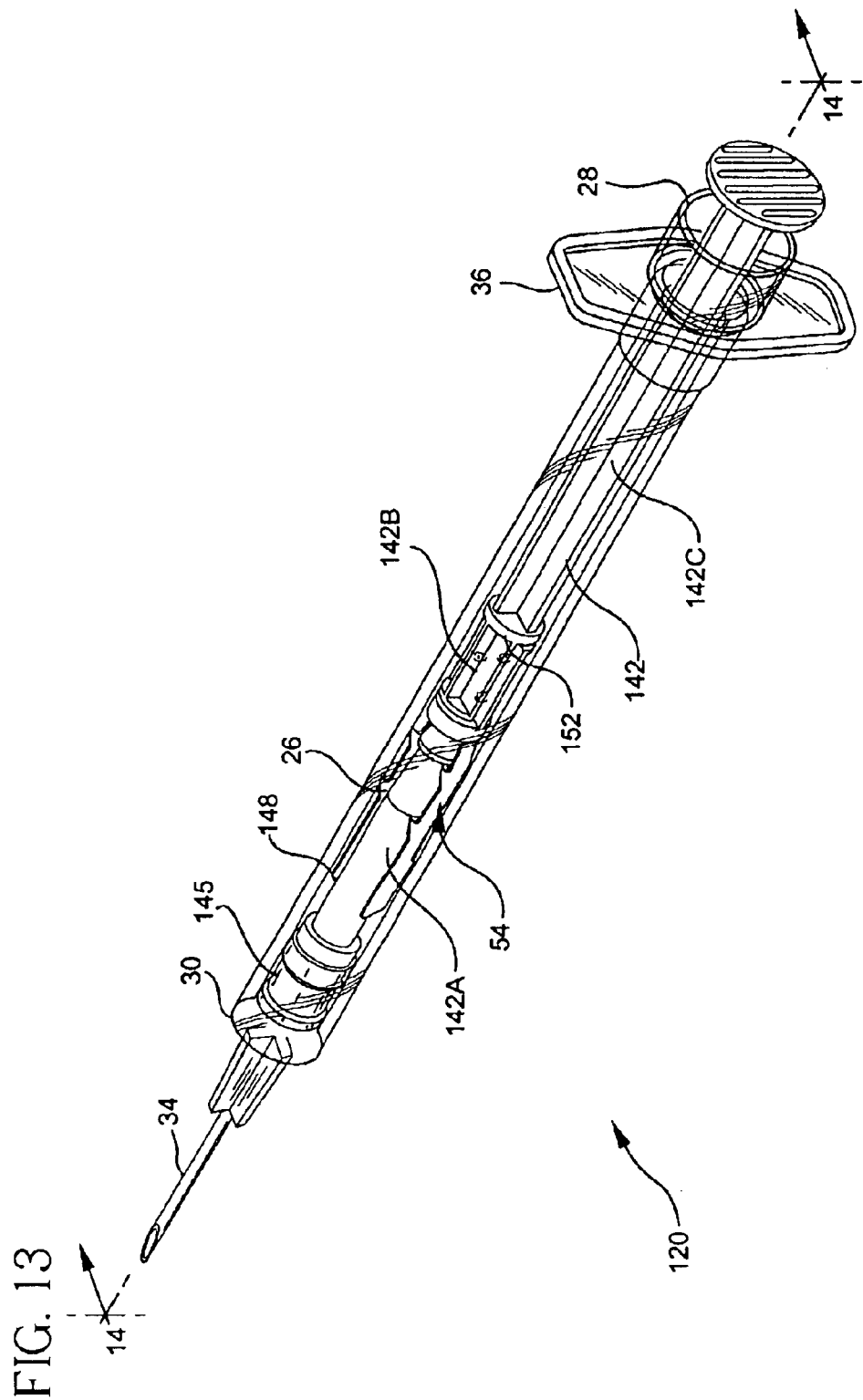
FIG. 13 is a perspective view of the alternative syringe assembly ready for use.
Figure 14:
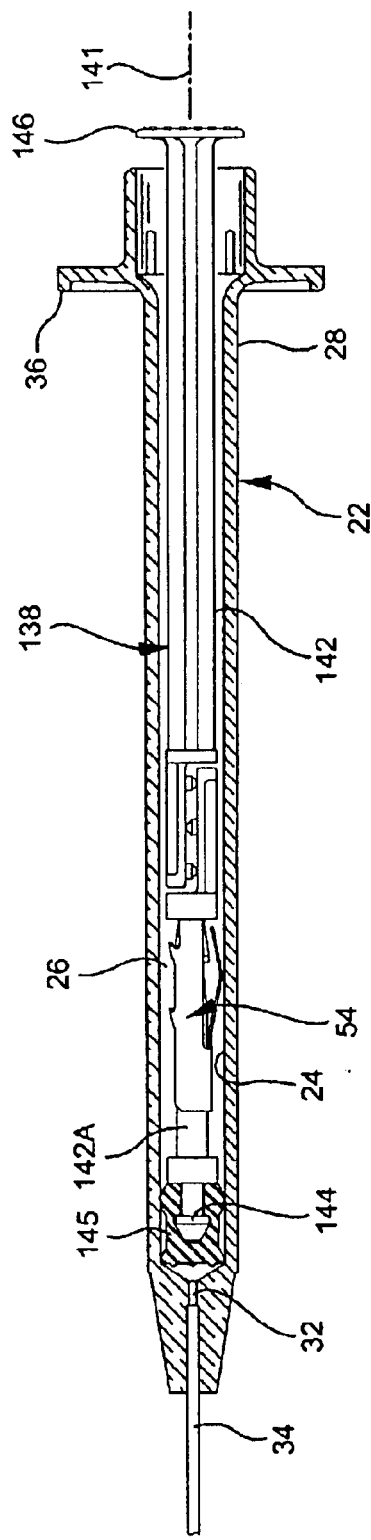
FIG. 14 is a cross-sectional view of the syringe assembly of FIG. 13 taken along line 14—14.
Figure 15:
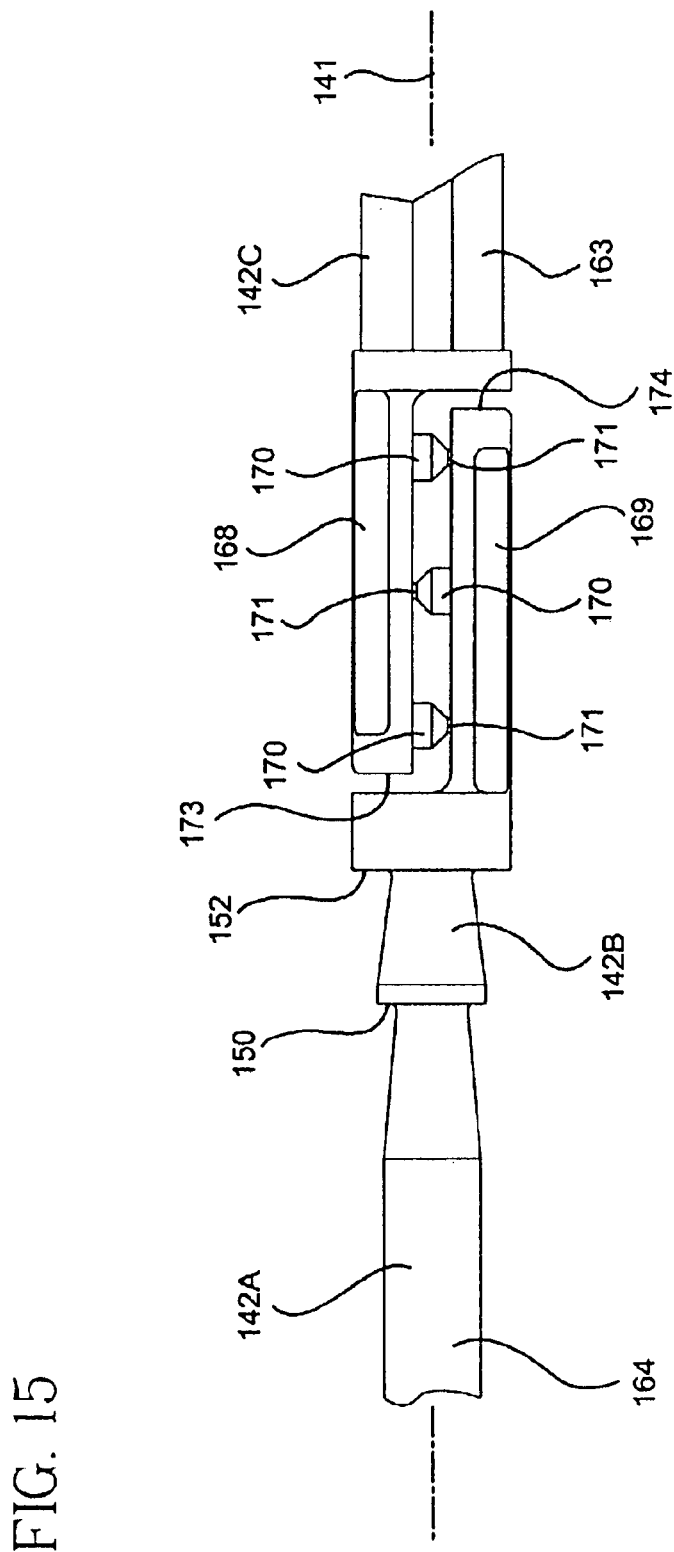
FIG. 15 is an enlarged partial side-elevational view illustrating the breakable connections on the plunger rod of the alternate syringe assembly.
Figure 16:
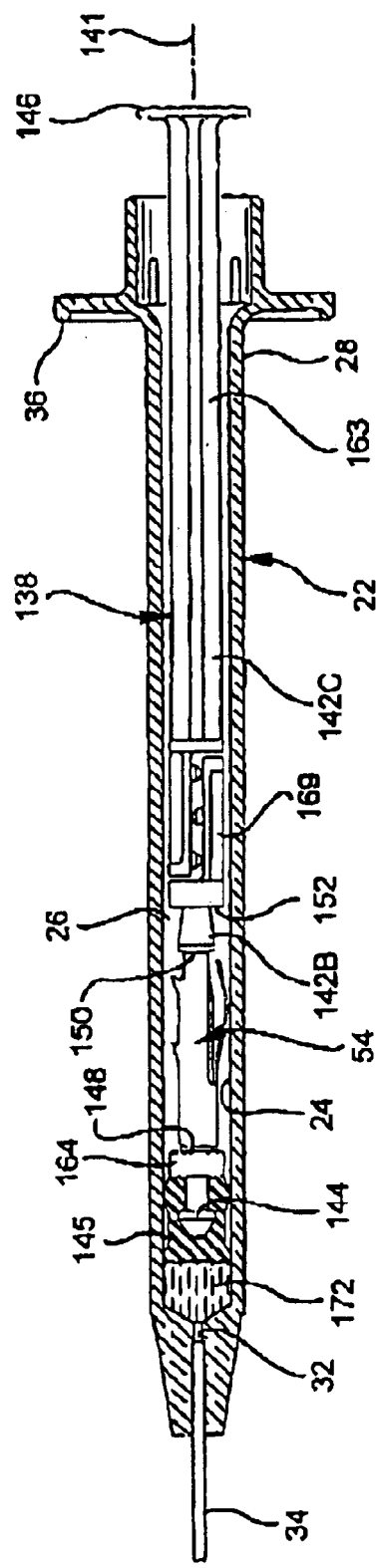
FIG. 16 is a cross-sectional side-elevational view illustrating the syringe assembly of FIG. 14 after being filled with liquid for injection.
Figure 17:
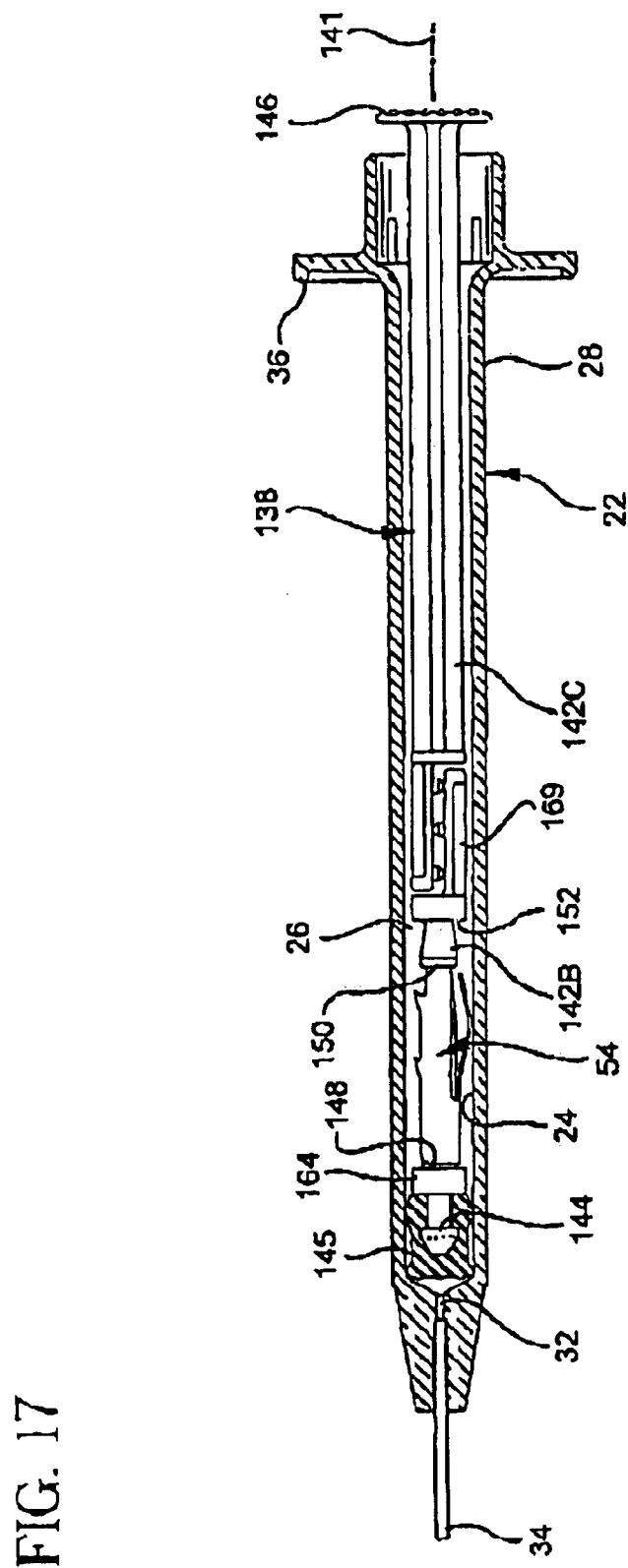
FIG. 17 is a cross-sectional side-elevational view illustrating the syringe assembly of FIG. 14 after the liquid has been injected.

A locking element 54 as used in the embodiment of FIGS. 1–11 is positioned within barrel 22. The locking element is generally trough-shaped. The locking element in this embodiment performs substantially similarly to the locking element of the embodiment of FIGS. 1–11. In use, the syringe assembly of this embodiment, as best illustrated in FIGS. 13 and 14, is used to draw liquid 172 through the lumen of the needle cannula into the chamber of the barrel as illustrated in FIG. 16. The liquid is then injected into a patient or other fluid transfer device and the syringe assembly, as best illustrated in FIG. 17, is disabled by virtue of locking element 54 preventing proximal motion of the plunger rod with respect to the barrel. At this time, the syringe may be discarded in a safe manner. However, at this point, there is a danger that someone may want to improperly re-use the syringe by applying excessive force to the plunger rod with respect to the barrel in an attempt to dislodge or damage the locking element to allow the plunger to again move freely with respect to the barrel. In order to prevent such an occurrence, the present embodiment provides a breakable connection separating the distal end and the proximal end of the plunger rod in order to prevent further use of the syringe as a result of the application of excessive forces to the plunger rod. In this embodiment, excessive forces to the plunger rod, especially along longitudinal axis 141 will cause the breakable connections to break, as best illustrated in FIG. 18, so that the proximal end of the plunger rod can no longer move the stopper and the assembly can no longer function as a syringe. The syringe barrel and plunger rod may be structured so that after the breakable connections break, the plunger rod may slide out of or fall out of the barrel.

Thus, it can be seen that the present invention provides a simple, reliable, easily fabricated, single use syringe which becomes inoperable and incapable of further use without any additional act on the part of the user. The present invention also provides a breakable plunger rod to help prevent the use of improper excessive force to the plunger rod from defeating the locking elements function.

What is claimed is:

1. A single use syringe assembly comprising:
   a barrel having an inside surface defining a chamber for retaining fluid, and open proximal end and a distal end having a passageway in communication with said chamber;
   a plunger rod assembly including an elongate body portion having a proximal end, a distal end, and a stopper on said elongate body portion proximate said distal end, said stopper being slidably positioned in substantially fluid-tight engagement with said inside surface of said barrel for drawing fluid into and out of said chamber by movement of said stopper relative to said barrel, said elongate body portion extending outwardly from said open proximal end of said barrel; and
   a generally trough-shaped locking element positioned within said barrel, said locking element defining a channel, said elongate body portion of said plunger rod assembly extending through said channel;
   one or more barbs extending from said locking element, said one or more barbs engaging said inside surface of said barrel for substantially preventing said locking element from moving proximally with respect to said barrel but allowing movement of said locking element towards said distal end;
   said locking element engaging said elongate body portion of said plunger rod assembly such that said locking element is movable towards said distal end of said barrel as said plunger rod assembly is advanced;
   a spring member attached to said locking element and urging said one or more barbs towards said inside surface of said barrel; and
   said proximal end and said distal end of said plunger rod being connected by a breakable connection, one of said proximal end and said distal end including an axial projection having at least one transverse protuberance projecting therefrom, said protuberance being connected to the other of said proximal portion and said distal portion, said breakable connection being on said protuberance, said breakable connection being strong enough to hold said proximal end and said distal end together during normal use of said syringe and breakable upon application of an additional force applied to said proximal portion along said longitudinal axis, said breakable connection being positioned proximally with respect to said locking element.

2. The syringe of claim 1 wherein said axial projection includes a plurality of transverse protuberances.

3. The syringe of claim 1 wherein said axial projection is planar shaped having a side wall and at least one transverse protuberance projecting from said side wall.

4. The syringe of claim 1 wherein said proximal portion, said distal portion and said breakable connection are integrally molded of plastic material.

5. The syringe of claim 1 wherein said breakable connection is made of material selected from the group consisting of polyethylene, polystyrene, polypropylene and adhesives.

6. The syringe of claim 1 wherein said stopper and said distal portion are integrally molded of plastic material.

7. The syringe of claim 1 further including means for preventing said breakable connection from breaking when said additional force is distally directed.

8. The syringe of claim 1 further including a cannula having a proximal end, a distal end and a lumen therethrough, said proximal end of said cannula being joined to elongate tip so that said lumen is in fluid communication with said passageway.

9. A single use syringe assembly comprising:
   a barrel having an inside surface defining a chamber for retaining fluid;
   a plunger rod assembly including an elongate body portion having a proximal end, a distal end and a stopper on said elongate body portion, said stopper being slidably positioned in substantially fluid-tight engagement with said inside surface of said barrel for drawing fluid into and out of said chamber by movement of said stopper relative to said barrel, said elongate body portion extending outwardly from said barrel;
   a locking element positioned within said barrel, said locking element including a base including first and second opposing walls and a third wall connecting said first and second walls, a first leg extending proximally from said first wall, a second leg extending proximally from said second wall, said first and second legs being in opposing relation, a first barb extending from said first leg and engaging said inside surface of said barrel, a second barb extending from said second leg and engaging said inside surface of said barrel, said first leg including a first end portion engageable with said elongate body portion of said plunger rod assembly, said second leg including a second end portion engageable with said elongate body portion of said plunger rod assembly, said first and second barbs being positioned to substantially prevent said locking element from moving proximally in said barrel, but allowing said locking element to move distally within said barrel; and
   said proximal end and said distal end of said plunger rod being connected by a breakable connection, one of said proximal end and said distal end including an axial projection having at least one transverse protuberance projecting therefrom, said protuberance being connected to the other of said proximal portion and said distal portion, said breakable connecting being on said protuberance, said breakable connection being strong enough to hold said proximal end and said distal end together during normal use of said syringe and breakable upon application of an additional force applied to said proximal portion along said longitudinal axis, said breakable connection being positioned proximally with respect to said locking element.

10. The syringe of claim 9 wherein said axial projection includes a plurality of transverse protuberances.

11. The syringe of claim 9 wherein said axial projection is planar shaped having a side wall and at least one transverse protuberance projecting from said side wall.

12. The syringe of claim 9 wherein said proximal portion, said distal portion and said breakable connection are integrally molded of plastic material.

13. The syringe of claim 9 wherein said breakable connection is made of material selected from the group consisting of polyethylene, polystyrene, polypropylene and adhesives.

14. The syringe of claim 9 wherein said stopper and said distal portion are integrally molded of plastic material.

15. The syringe of claim 9 further including means for preventing said breakable connection from breaking when said additional force is distally directed.

16. The syringe of claim 9 further including a cannula having a proximal end, a distal end and a lumen threthrough, said proximal end of said cannula being joined to elongate tip so that said lumen is in fluid communication with said passageway.

17. A single use syringe as described in claim 9 including means for resiliently urging said first and second barbs towards said inside surface of said barrel.

18. A single use syringe as described in claim 17 wherein said means for resiliently urging including a third leg extending proximally from said third wall of said base, each of said first and second legs includes a substantially flat body having an inner edge substantially adjacent to said third leg and an outer edge, said first and second barbs extending, respectively, from said outer edges of said first and second legs.

19. A single use syringe as described in claim 18 wherein said locking element has a generally trough-shaped configuration.

20. A single use syringe as described in claim 19 wherein said elongate body portion of said plunger rod assembly includes first and second adjoining portions, said first portion being distal of said second portion and having a smaller diameter than said second portion, a first shoulder separating said first and second portions, and a stop surface at the distal end of said first portion, said first ands second inwardly extending end portion of said first and second legs being engageable with said first shoulder, said locking element being engageable with said stop surface.

* * * * *